(12) United States Patent
Li

(10) Patent No.: US 7,280,222 B2
(45) Date of Patent: Oct. 9, 2007

(54) COMPACT OPTICAL APPARATUS

(76) Inventor: Chian Chiu Li, 1847 Bristol Bay CMN, San Jose, CA (US) 95131-3802

( * ) Notice: Subject to any disclaimer, the term of this patent is extended or adjusted under 35 U.S.C. 154(b) by 35 days.

(21) Appl. No.: 11/160,948

(22) Filed: Jul. 16, 2005

(65) Prior Publication Data

US 2005/0243327 A1    Nov. 3, 2005

Related U.S. Application Data

(62) Division of application No. 10/367,510, filed on Feb. 14, 2003, now Pat. No. 7,023,563.

(51) Int. Cl.
*G01B 11/02* (2006.01)
(52) U.S. Cl. .................................... 356/497
(58) Field of Classification Search ................ 356/479, 356/496, 497, 503, 504
See application file for complete search history.

(56) References Cited

U.S. PATENT DOCUMENTS

| | | | |
|---|---|---|---|
| 5,321,501 A | 6/1994 | Swanson et al. | |
| 5,459,570 A * | 10/1995 | Swanson et al. | 356/479 |
| 5,742,419 A | 4/1998 | Dickensheets et al. | |
| 6,028,669 A * | 2/2000 | Tzeng | 356/504 |
| 6,148,016 A | 11/2000 | Hegblom | |
| 6,301,035 B1 | 10/2001 | Schairer | |
| 6,320,686 B1 | 11/2001 | Schairer | |
| 6,392,756 B1 * | 5/2002 | Li et al. | 356/632 |
| 6,552,797 B2 * | 4/2003 | Swanson | 356/479 |
| 6,687,014 B2 * | 2/2004 | Zaidi et al. | 356/504 |
| 6,721,503 B1 | 4/2004 | Jokerst | |
| 6,775,007 B2 * | 8/2004 | Izatt et al. | 356/497 |

* cited by examiner

*Primary Examiner*—Gregory J. Toatley, Jr.
*Assistant Examiner*—Michael A. Lyons

(57) ABSTRACT

In a compact optical device, a light emitting area of a light source and a light sensing area of a detector are placed in proximity. The detector receives part of a beam which is reflected back to the source from a sample. As a result, a beam splitter is no longer needed. By eliminating the beam splitter and packing the light source and detector in closeness, dimensions of the optical device are reduced.

20 Claims, 2 Drawing Sheets

Figure 2:
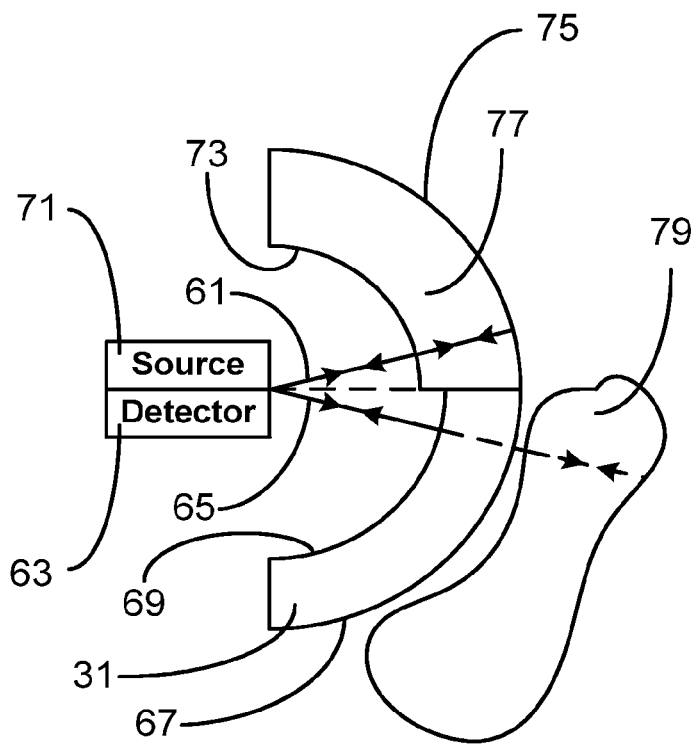

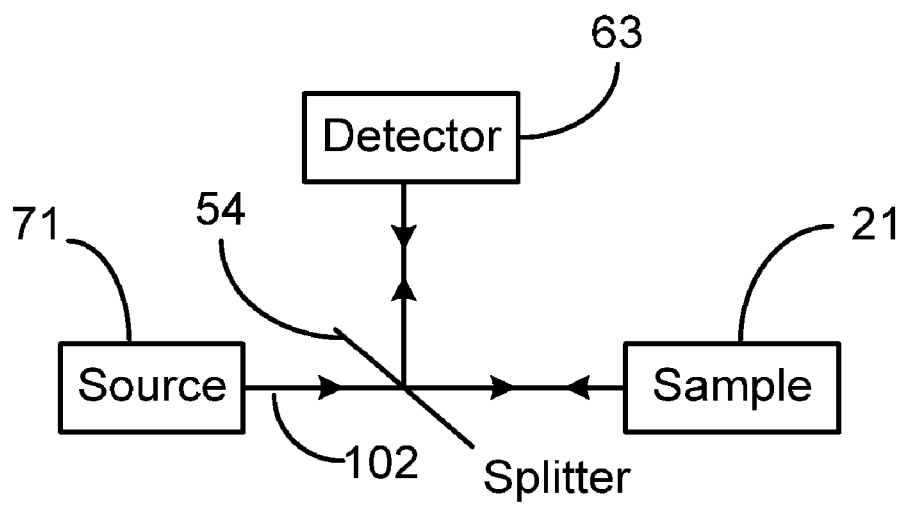
FIG. 1-A (*Prior Art*)
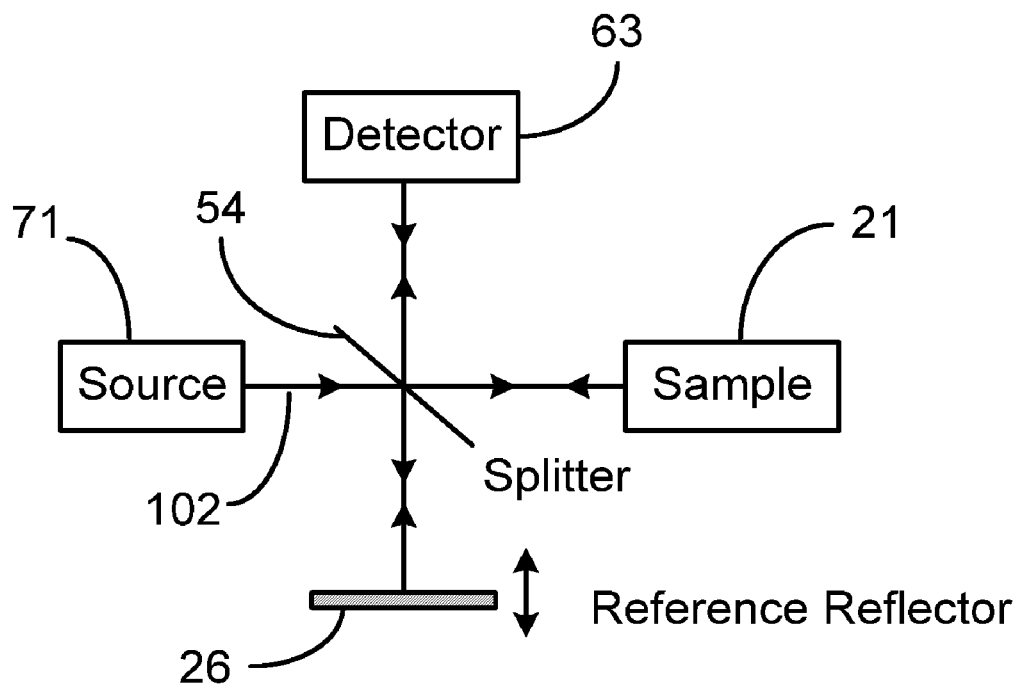
FIG. 1-B (*Prior Art*)

COMPACT OPTICAL APPARATUS

CROSS REFERENCE TO RELATED APPLICATION

This is a division of Ser. No. 10/367,510, filed Feb. 14, 2003, now U.S. Pat. No. 7,023,563, issued 2006 Apr. 4.

BACKGROUND

1. Field of Invention

This invention is related to optical devices, particularly to optical devices having a compact structure.

2. Description of Prior Art

Optical devices are closely related to industry, medical field, and our daily life. As we know, light is frequently used to measure characteristics of materials and devices, investigate biological samples, and read and record information in an optical disc, such as a compact disc (CD) or a digital versatile disc (DVD). There is a need for a small device size or a miniature device in many applications. For example, optical coherence tomography (OCT) is an optical imaging technology capable of measuring three-dimensional structures of highly scattering biological tissues. A doctor is able to observe beneath a patient's skin using an OCT. Currently, OCT system is bulky and expensive. A miniature OCT will lower the cost and make it possible for a portable or even disposable device, which in turn would expand OCT applications greatly.

External dimensions of an optical device depend upon its opto-mechanical structure, which is determined by the optical structure. An optical device basically comprises a light source, a detector, and other optical components. The light source generates a light beam which is transmitted along an optical path. The detector receives a signal beam which is transmitted through another path. Usually, the two paths overlap partially and are connected by a beam splitter such that they can share some components to make the device compact. In an optical measurement device, for example, a beam from a light source is focused onto a sample by a focusing lens and reflected back, the reflected beam is collected by the focusing lens, and transmitted to a detector. Since the light source and the detector are discrete devices which are disposed in two locations, a beam splitter is needed to split an optical path from the sample to the source, such that part of the reflected beam can follow another path to reach the detector.

Accordingly, there exists a need to reduce or further reduce the size of an optical device; a current optical device, however, consists of at least three components: a light source, a detector, and a beam splitter, which sets a limit for dimension reduction.

OBJECTS AND ADVANTAGES

Accordingly, several main objects and advantages of the present invention are:

a). to provide an improved optical device;

b). to provide such a device which is smaller in size;

c). to provide such a device which has less component count; and d). to provide such a device in which a light source and a detector are placed closely and a light-emitting area of the light source and a light sensing area of the detector are arranged in proximity.

Further objects and advantages will become apparent from a consideration of the drawings and ensuing description.

SUMMARY

In accordance with the present invention, a compact optical device is constructed. In the device, a light source and a detector are placed close to each other. A beam emitted by the light source impinges onto a sample and is reflected back. The reflected beam is received by the detector directly because two optical paths—from the source to the sample and from the sample to the detector—are in proximity. As a consequence of this, a beam splitter is no longer needed. The device size, therefore, is reduced by less components and the closely packed light source and detector.

ABBREVIATIONS

AR Anti-reflection
CD Compact Disc
DVD Digital Versatile Disc
HR High Reflection
OCT Optical Coherence Tomography

DRAWING FIGURES

FIG. 1-A is a schematic diagram showing a prior-art optical device.

FIG. 1-B is a schematic diagram showing a prior-art OCT structure.

Figure 3:
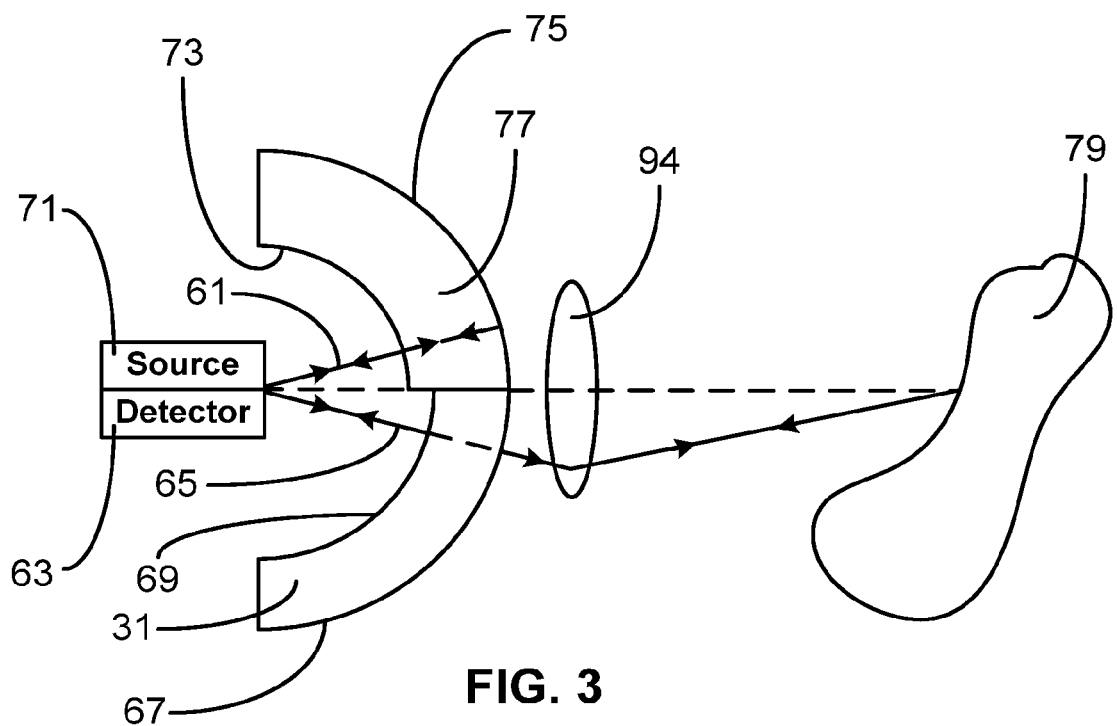

FIGS. 2 and 3 are schematic diagrams illustrating embodiments of OCT systems having a simpler and more compact structure than the current ones according to the invention.

REFERENCE NUMERALS IN DRAWINGS

| | | | |
|---|---|---|---|
| 21 | sample | 26 | reflector |
| 31 | element | 54 | beam splitter |
| 61 | beam portion | 63 | detector |
| 65 | beam portion | 67 | AR coating |
| 69 | AR coating | 71 | light source |
| 73 | AR coating | 75 | HR coating |
| 77 | modulator element | 79 | sample |
| 94 | lens system | 102 | beam |

DETAILED DESCRIPTION—FIGS. 1-A AND 1-B—PRIOR-ART OPTICAL DEVICES

FIG. 1-A shows schematically a prior-art optical device. A light source 71 emits a beam 102. Beam 102 is transmitted to impinge onto a sample 21 after passing through a beam splitter 54. A reflected beam from sample 21 is then reflected by splitter 54 and is transmitted to a detector 63. The optical device contains three components: light source 71, detector 63, and splitter 54.

FIG. 1-B shows schematically another prior-art optical device, an OTC system. The OCT system adds an adjustable reference reflector 26 to the setup of FIG. 1-A. Reflector 26 receives a portion of beam 102 which is reflected by splitter 54 and reflects it back. The reflected beam from reflector 26 is transmitted through splitter 54 and reaches detector 63. Thus detector 63 detects interference between two beams, one from sample 21 and the other from reflector 26. In an OCT, light source 71 is usually of low-coherence type. Through changing positions of reflector 26, series of low-coherence interference are collected and analyzed to derive layered structure of sample 21. Again, the OCT in FIG. 1-B needs splitter 54, besides source 71, detector 63, and reflector 26.

FIGS. 2 AND 3—OCT SYSTEMS WITH A RELATIVELY SIMPLE AND COMPACT STRUCTURE

FIGS. 2 and 3 depict schematically embodiments of OCT systems which have a simpler and more compact structure than the current OCTs. As shown in FIG. 2, light source 71 is placed adjacent to detector 63. Two elements 77 and 31 form a spatial phase modulator. Element 31 mainly works as a protective shield. The two elements divide a beam emitted by light source 71 into two portions, 61 and 65. Element 77 has two surfaces coated with an anti-reflection (AR) coating 73 and a high reflection (HR) coating 75 respectively. Portion 61 enters element 77 and is reflected back by HR coating 75. Element 77 is designed with such a shape that coating 75 reflects beam portion 61 back to light source 71 with a uniform phase retardation over its wavefront. Element 31 has two surfaces coated with AR coatings 67 and 69. Beam portion 65 passes through element 31, encounters a sample 79, and is reflected by the sample. Element 31 is designed to give beam portion 65 a uniform phase retardation. Being reflected by sample 79, part of portion 65 converges to source 71.

Assume detector 63 and light source 71 are arranged so that the detector's light detecting area (not shown in FIG. 2) and the source's light emitting area (not shown in FIG. 2) are in proximity. If the detecting and emitting areas are close enough to each other, detector 63 may share the light which is reflected back to the source. In other words, detector 63 may receive the reflected portions 61 and 65 directly, and detect interference between them, which also means a beam splitter is no longer in need. As a result of deleting the beam splitter and placing the light source and detector in proximity, the OCT has a simpler and more compact structure, and a smaller size. For the OCT system, HR coating 75 serves as a reference reflector. Element 77 may contain electro-optical materials to tune phase retardation of portion 61 electrically, or have a structure to adjust the phase retardation mechanically.

If sample 79 has a HR surface, interference signals received by detector 63 represent a value which is averaged over the measured surface area. If sample 79 is a highly scattering medium, the reflected portion 65 contains reflection from both surface and inside the medium. In such a case, low-coherence interference signals are needed to analyze the medium. For the system, element 77 and HR coating 75 define a reference optical path length for beam portion 61. The interference signals reveal information of one region of sample 79, which region generates a matching sample optical path length to the reference optical path length.

To increase measurement distance for the scheme of FIG. 2, a lens system 94 is brought in to the setup as shown schematically in FIG. 3. Without the lens system, sample 79 has to be placed close to element 31 so that the reflected beam has an adequate intensity. With a lens system, the sample can be away at a distance from the element. The lens system can also be placed between light source 71 and the element.

CONCLUSION, RAMIFICATIONS, AND SCOPE

Accordingly, the reader will see that when a light emitting area of a light source and a light sensing area of a detector are placed in proximity, a reflected beam from a sample reaches the source and detector simultaneously. Therefore a beam splitter is no longer needed. Through reducing component count and packing a light source and detector in closeness, dimensions of the resulting optical device are reduced.

Although the description above contains many specificities, these should not be construed as limiting the scope of the invention but as merely providing illustrations of some of the presently preferred embodiments. Numerous modifications, alternations, and variations will be obvious to those skilled in the art. First, a beam can be divided by a spatial phase modulator into portions of any number with any geometrical shapes by wavefront-division; for example, a beam can be divided into a central circular portion and several outer ring-shaped portions. Second, the intensity ratio of one portion to another can be of any value depending upon the interference effect between them. In FIG. 2, for example, if the reflected beam from sample 79 has a low intensity, portion 65 should have a larger intensity than portion 61 to improve the contrast of interference patterns.

Therefore the scope of the invention should be determined by the appended claims and their legal equivalents, rather than by the examples given.

What is claimed is:

1. A method for optical measurements, comprising:
   1) causing a light source to generate a first beam;
   2) arranging said first beam to impinge onto a medium for generating a signal beam in a direction toward said light source; and
   3) sensing said signal beam by a detector;
   4) said source and said detector being arranged such that at least one entire beam of said first and signal beams is disposed substantially proximate to the other beam directly and said first and signal beams share optics where they are substantially proximate.

2. The method according to claim 1, further including partially returning said first beam for generating a reference beam, said reference beam being transmitted to said detector for producing interference between said reference and said signal beams.

3. The method according to claim 2, further including adjusting the phase difference between said signal and reference beams.

4. The method according to claim 1 wherein said source has relatively low coherence.

5. The method according to claim 1, further including focusing said first beam onto said medium.

6. The method according to claim 1, wherein said source and said detector are disposed in a side-by-side arrangement.

7. The method according to claim 1, wherein said source and said detector are disposed such that said source and said detector are in proximity.

8. The method according to claim 1, wherein said source and said detector are integrated monolithically.

9. The method according to claim 1, wherein said signal and said first beams are arranged such that they at least partially overlap.

10. An optical device comprising:
    1) a light source having a light emitting area for generating a first beam toward a predetermined direction; and 2) a detector having a light detecting area, said detecting region facing said predetermined direction to receive a second beam;
3) said light source and said detector being arranged such that said emitting and detecting areas are side-by-side and in proximity,
4) said emitting and detecting areas being arranged in such proximity that at least an entire first portion of said first beam and an entire second portion of said second beam are disposed substantially proximate to each other directly, and said first and second beams share optics where they are substantially proximate, wherein said first and second portions are connected directly to said emitting and detecting areas, respectively.

11. The optical device according to claim 10 wherein said source and said detector are disposed such that said first and second beams are in proximity.

12. The optical device according to claim 10 wherein said source and said detector are integrated monolithically.

13. An optical device comprising:
1) a light source having a light emitting area for generating a first beam, said first beam being transmitted through a predetermined first optical path; and
2) a detector having a light detecting area for sensing a signal beam, said signal beam being transmitted through a predetermined second optical path;
3) said source and said detector being arranged such that said light emitting and detecting areas are side-by-side and at least one entire path of said first and second paths is disposed in substantial proximity to the other path directly and said first and second paths share optics where they are substantially proximate.

14. The optical device according to claim 13 wherein said source and said detector are disposed such that said emitting and detecting areas are in proximity.

15. The optical device according to claim 13 wherein said source and said detector are integrated monolithically.

16. The optical device according to claim 13 wherein said first beam is arranged to impinge onto a first medium for generating said signal beam.

17. The optical device according to claim 16, further including a second medium for returning a portion of said first beam for generating a reference beam, said reference beam being transmitted to said detector for producing interference between said reference and said signal beams.

18. The optical device according to claim 16, further including lens means for focusing said first beam onto said first medium.

19. The optical device according to claim 13 wherein said signal and said first beams are arranged such that they at least partially overlap.

20. The optical device according to claim 13 wherein said source has relatively low coherence.

* * * * *